US00PP26876P2

(12) United States Plant Patent
Frangi

(10) Patent No.: US PP26,876 P2
(45) Date of Patent: Jun. 28, 2016

(54) ***LAGERSTROEMIA* PLANT NAMED 'MILABLA'**

(50) Latin Name: *Lagerstroemia indica*
Varietal Denomination: Milabla

(71) Applicant: Piero Frangi, Barlassina (IT)

(72) Inventor: Piero Frangi, Barlassina (IT)

(73) Assignee: Fondazione Minoprio, Como (IT)

( * ) Notice: Subject to any disclaimer, the term of this patent is extended or adjusted under 35 U.S.C. 154(b) by 69 days.

(21) Appl. No.: 14/544,046

(22) Filed: Nov. 19, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

PLUTO Plant Variety Database Mar. 17, 2016.p. 1.*

* cited by examiner

*Primary Examiner* — Annette Para
(74) *Attorney, Agent, or Firm* — Penny J. Aguirre

(57) ABSTRACT

A new cultivar of *Lagerstroemia indica* plant named 'Milabla' that is characterized by its well-branched plant habit, its early and long lasting bloom period, its flowers that are white in color, its good tolerance to powdery mildew, and its good frost resistance.

2 Drawing Sheets

Botanical classification: *Lagerstroemia indica.*
Variety denomination: 'Milabla'.

CROSS REFERENCE TO RELATED APPLICATIONS

This application is co-pending with a U.S. Plant Patent Applications filed for plants derived from the Inventor's breeding program that are entitled *Lagersiroemia* Plant Named 'Milavio' (U.S. Plant patent application Ser. No. 14/544,052 ), 'Milarosa' (U.S. Plant patent application Ser. No. 14/544,050), 'Milarosso' (U.S. Plant patent application Ser. No. 14/544,051), and 'Milaperl' (U.S. Plant patent application Ser. No. 14/544,053).

BACKGROUND OF THE INVENTION

The present invention relates to a new and distinct cultivar of *Lagerstroemia indica*. The new *Lagerstroemia* will hereafter by its cultivar name, 'Milabla'. 'Milabla' is a new cultivar of deciduous shrub grown for use as an ornamental landscape plant.

The new cultivar of *Lagerstroemia* is the result of a controlled breeding program conducted by the Inventor in Vertemate con Minoprio, Italy. 'Milabla' originated as a seedling that arose from seeds that were pooled and sown in 1998 from open pollination of 33 unnamed and unpatented proprietary plants in the Inventor's breeding program, designated as breeding line No. 3.32. 'Milabla' was selected as a single unique plant in 1999 from amongst the resulting seedlings. The exact parent plants are unknown.

Asexual propagation of the new cultivar was first accomplished by the Inventor using stem cuttings in 1999 in Vertemate con Minoprio, Italy. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Milabla' as a unique cultivar of *Lagerstroemia.*

1. 'Milabla' exhibits a well-branched plant habit.
2. 'Milabla' exhibits an early and long lasting bloom period, flowering from the beginning of July to the end of August in Northern Italy.
3. 'Milabla' exhibits flowers that are white in color.
4. 'Milabla' exhibits good tolerance to powdery mildew.
5. 'Milabla' exhibits good frost resistance; withstanding temperatures at least as low as −15° C.

'Milabla' can be most closely compared to *Lagerstroemia* indica cultivars that arose from the same breeding program. 'Milarosso', 'Milaperl', 'Milarosa', and 'Milavio'. 'Milarosso' differs from 'Milabla' in having flowers that are dark pink in color. 'Milaperl' differs from 'Milabla' in having flowers that are pale pink in color. 'Milarosa' differs from 'Milabla' in having flowers that are pink in color. 'Milavio' differs from 'Milabla' in having flowers that are violet in color.

BRIEF DESCRIPTION OF THE DRAWINGS

The accompanying colored photographs illustrate the overall appearance and distinct characteristics of the new *Lagerstroemia*. The photographs were taken of a plant two years in age as grown outdoors in a 2-liter container in Zundert, The Netherlands.

The photograph in FIG. 1 provides a side view of 'Milabla' in bloom.

Figure 1:
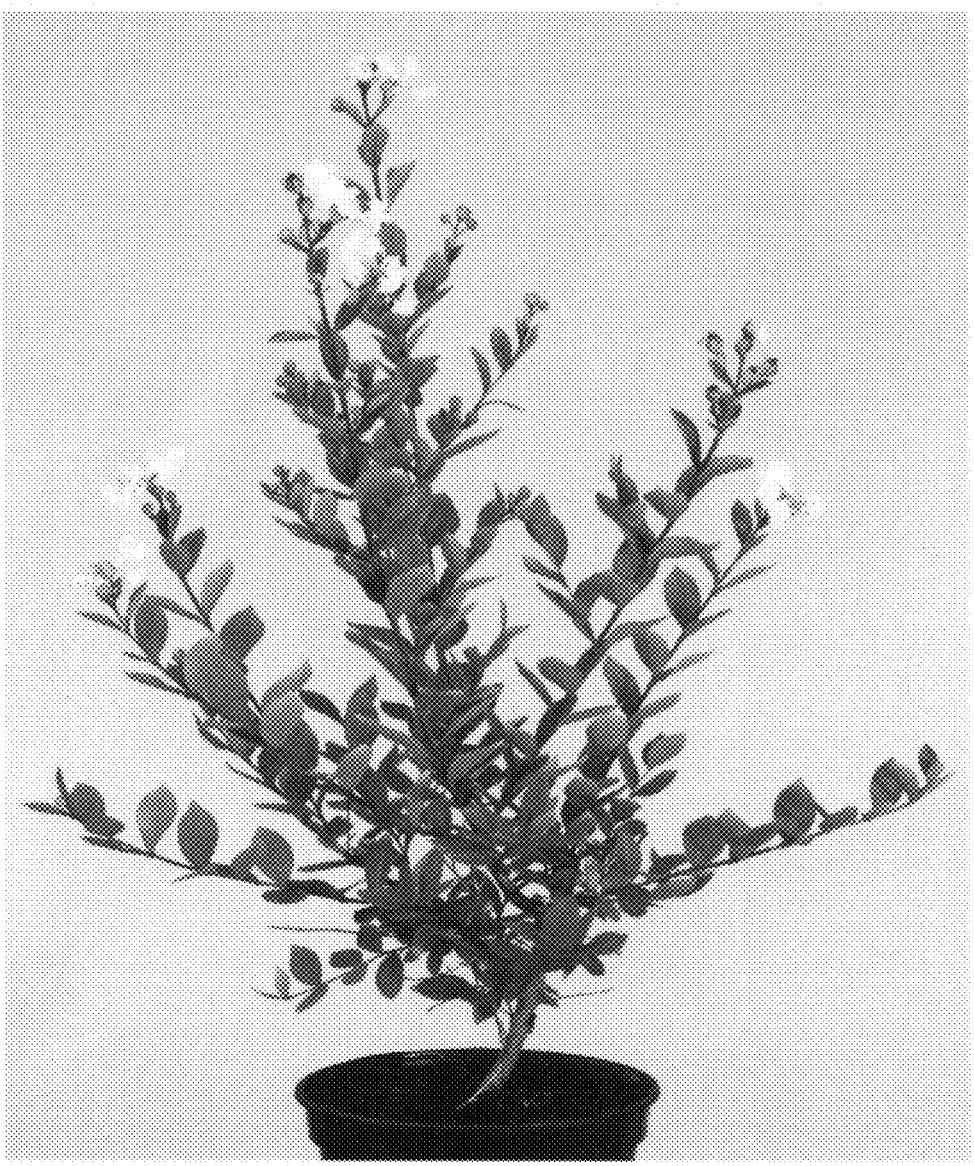
Figure 2:
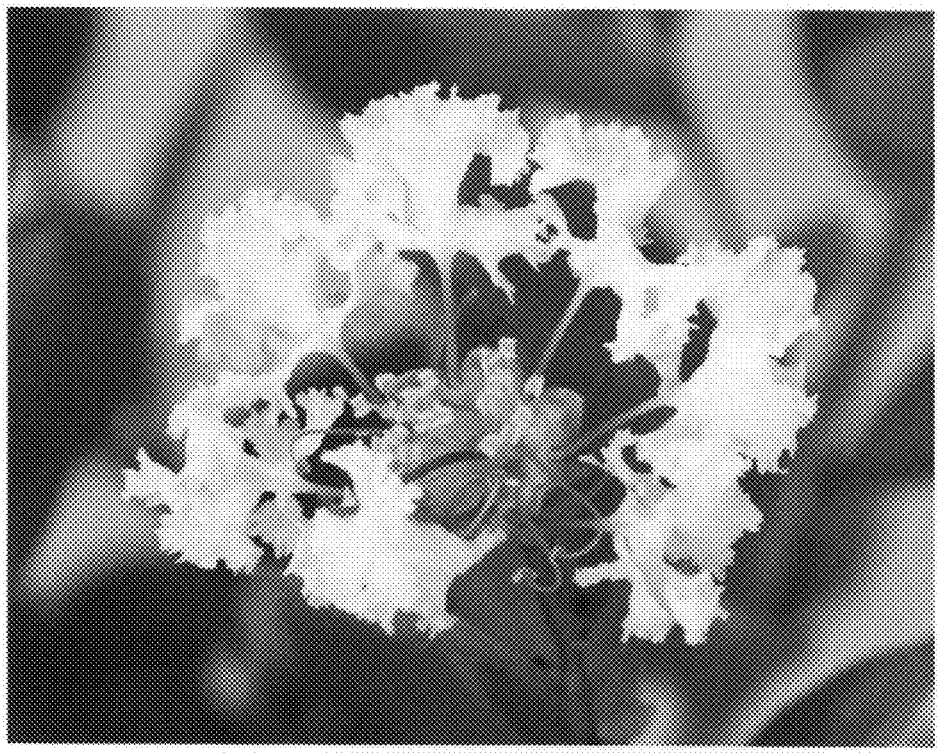

The photograph in FIG. 2 provides a close-up view of the inflorescences of 'Milabla'.

Figure 3:
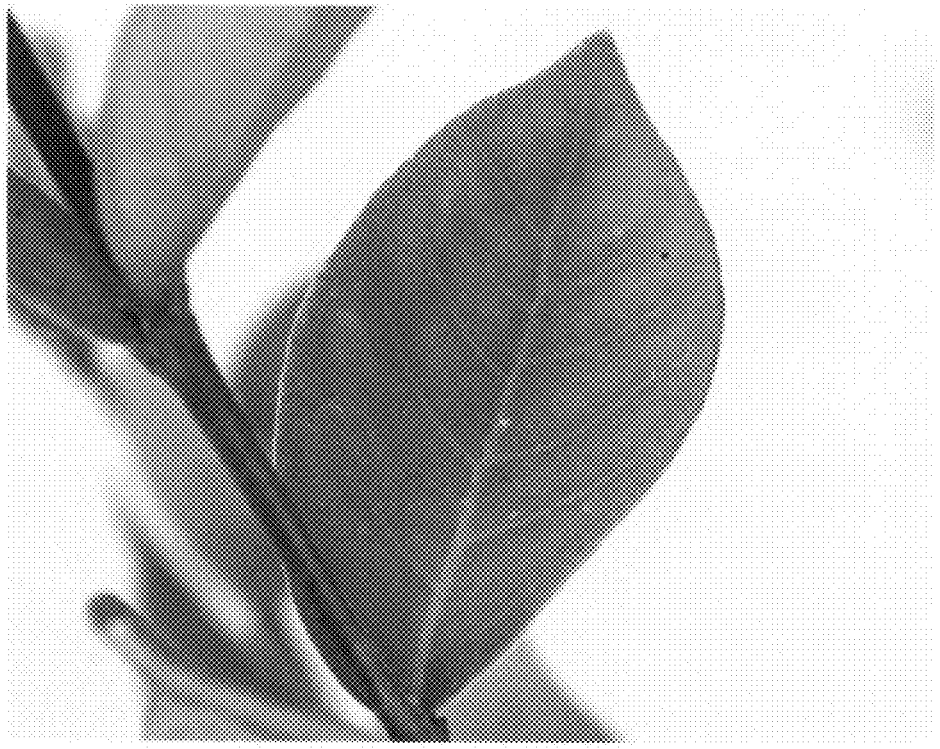

The photograph in FIG. 3 provides a close-up view of a leaf of 'Milabla'.

The colors in the photographs are as close as possible with the digital photography techniques available, the color values cited in the detailed botanical description accurately describe the colors of the new *Lagerstroemia*.

DETAILED BOTANICAL DESCRIPTION

The descriptions were taken of plants two years in age as grown outdoors in 2-liter containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early and long blooming; from early July to the end of August in Northern Italy.

*Plant type*.—Deciduous shrub.

*Plant habit*.—Well-branched and upright.

*Height and spread*.—An average of 54.4 cm in height and 43.0 cm in spread for a two year-old plant as grown in a 2-Liter container.

*Cold hardiness*.—At least to U.S.D.A. Zone 8a.

*Frost resistance*.—Good; withstanding temperatures at least as low as −15° C.

*Diseases*.—Good tolerance to powdery mildew caused by *Erysiphe lagerstroemia* has been observed.

*Root description*.—Fibrous and fine.

*Root development*.—Roots in 6 weeks and fully develops in a 9-cm container in about 4 months.

*Propagation*.—Stem cuttings.

*Growth rate*.—Moderate.

Stem description:

*Shape*.—Quadrangulate with rounded wings.

*Stem color*.—A blend between 174A and 177B with wings N170A.

*Stem size*.—An average of 21.7 cm in length and 3 mm in diameter.

*Stem surface*.—Slightly glossy.

*Stem strength*.—Strong.

*Branching*.—An average of 15 lateral branches, freely branching.

*Internode length*.—An average of 2.5 cm.

Foliage description:

*Leaf shape*.—Elliptic.

*Leaf division*.—Single.

*Leaf base*.—Attenuate.

*Leaf apex*.—Acute.

*Leaf venation*.—Pinnate, color; upper surface 144B to 144C, lower surface 147D.

*Leaf margins*.—Entire, slightly undulate.

*Leaf arrangement*.—Opposite to nearly opposite.

*Leaf attachment*.—Petiolate.

*Leaf surface*.—Both surfaces moderately covered with glands, minute in size, and colored the same as the leaf surface.

*Leaf size*.—An average of 4.2 cm in length and 2.3 cm in width.

*Leaf quantity*.—An average of 18 (9 pairs) per branch.

*Leaf color*.—Young leaves upper surface; 143B, young leaves lower surface; 144B, mature growth upper surface; a blend between 145A and 147D, mature growth lower surface; 144B to 144C.

*Leaf fragrance*.—Fragrance typical for Lagerstroemia detected when touched.

*Petioles*.—An average of 1 mm in length and width and 147D in color, slightly glossy surface.

Flower description:

*Inflorescence type*.—Terminal thyrse.

*Lastingness of inflorescence*.—About one week.

*Inflorescence size*.—An average of 6.6 cm in height and 6.8 cm in width.

*Inflorescence number*.—An average of 2 per lateral stem.

*Flower number*.—An average of 7 flowers per inflorescence.

*Flower fragrance*.—Moderately strong sweet scent.

*Flower buds*.—Flattened globular in shape, an average of 8 mm in diameter and 7 mm in depth, surface; glabrous, color; 145B with margins on immature sepals 174A to 174B.

*Flower aspect*.—Upright to outward.

*Flower type*.—Rotate.

*Flower size*.—An average of 5.0 cm in diameter and 2.4 mm in depth.

*Petals*.—An average of 6, reniform in shape, strongly undulate bidentate margins, stalked base, praemorse apex, both surfaces glabrous and dull, an average of 2.2 cm in length and 1.7 cm in width, color when opening and when fully open upper and lower surface; NN155D with stalk 51B, petal color does not fade.

*Calyx*.—Rotate in shape, an average of 1 cm in length and diameter.

*Sepals*.—An average of 6 petals, rotate arrangement, fused at base, rhomboidal in shape, entire margins, acuminate apex, both surfaces smooth and dull, an average of 1 mm in length and 4 mm in width, color; upper and lower surface when opening and when fully open a blend between 144D and 151D.

*Peduncles*.—Strong, an average of 3.9 cm in length and 1.5 mm in width, 174B in color, surface is slightly glossy, main peduncles held at an average angle of 0° to the lateral branch, secondary peduncles held at an average angle of 50° to the lateral branch.

*Pedicels*.—Strong, an average of 8 mm in length and 1 mm in width, 185C to 185D in color, main pedicels held at an average angle of 0° to the lateral branch, secondary pedicels held at an average angle of 30° to the lateral branch.

Reproductive organs:

*Stamens*.—Average of 40, anther; an average of 2 mm in length, dorsifixed, narrow oblong in shape, 165B in color, filament; an average of 1.3 cm in length and 145D in color, pollen is moderate in quantity and 9B in color.

*Pistils*.—An average of 1, an average of 1.8 cm in length, style; an average of 1.7 cm in length and 179B in color, stigma is club-shaped and 144A in color, ovary is 151D in color.

*Seed and fruit*.—None observed.

It is claimed:

1. A new and distinct cultivar of *Lagerstroemia* plant named 'Milabla' as herein illustrated and described.

* * * * *